(12) United States Patent
Shinton et al.

(10) Patent No.: US 12,745,340 B2
(45) Date of Patent: Sep. 22, 2026

(54) RF SOURCE

(71) Applicant: Elekta Limited, Crawley (GB)

(72) Inventors: Ian Shinton, Crawley (GB); Peter Doherty, Crawley (GB); Emma Woolridge, Crawley (GB); Ana Rita Pereira Morgado Da Silva, Crawley (GB)

(73) Assignee: Elekta Limited, Crawley (GB)

( * ) Notice: Subject to any disclaimer, the term of this patent is extended or adjusted under 35 U.S.C. 154(b) by 166 days.

(21) Appl. No.: 18/716,048

(22) PCT Filed: Dec. 2, 2022

(86) PCT No.: PCT/EP2022/084282
§ 371 (c)(1),
(2) Date: Jun. 3, 2024

(87) PCT Pub. No.: WO2023/099762
PCT Pub. Date: Jun. 8, 2023

(65) Prior Publication Data

US 2025/0040024 A1 Jan. 30, 2025

(30) Foreign Application Priority Data

Dec. 3, 2021 (GB) ..................................... 2117515

(51) Int. Cl.

| | |
|---|---|
| ***H05H 7/02*** | (2006.01) |
| ***A61N 5/10*** | (2006.01) |
| ***G21K 5/04*** | (2006.01) |

(52) U.S. Cl.
CPC ............. *H05H 7/02* (2013.01); *A61N 5/1081* (2013.01); *G21K 5/04* (2013.01);
(Continued)

(58) Field of Classification Search
CPC ............... H05H 7/02; H05H 2007/022; H05H 2007/025; H05H 2007/027; H05H 7/22;
(Continued)

(56) References Cited

U.S. PATENT DOCUMENTS

| | | | |
|---|---|---|---|
| 10,413,751 B2 * | 9/2019 | Dempsey | A61N 5/1039 |
| 2010/0219776 A1 * | 9/2010 | Liu | H05H 7/02 315/501 |

(Continued)

FOREIGN PATENT DOCUMENTS

| | | | |
|---|---|---|---|
| CN | 200987235 Y | 12/2007 | |
| DE | 102012209185 B4 * | 5/2019 | A61N 5/10 |

(Continued)

OTHER PUBLICATIONS

Translation of DE 102012209185 B4 (Year: 2019).*
(Continued)

*Primary Examiner* — Renan Luque
(74) *Attorney, Agent, or Firm* — Schwegman Lundberg & Woessner, P.A.

(57) ABSTRACT

Disclosed here is an RF source comprising first, and second RF pulse generators arranged to deliver RF pulses for a particle accelerator and a controller arranged to control the first and second RF pulse generators to generate pulses sequentially.

20 Claims, 16 Drawing Sheets

(52) U.S. Cl.
CPC ................ *A61N 2005/1089* (2013.01); *H05H 2007/022* (2013.01); *H05H 2007/025* (2013.01)

(58) Field of Classification Search
CPC .................... H05H 9/00; A61N 5/1081; A61N 2005/1089; A61N 5/1049; G21K 5/04; H03B 9/10; H01J 25/50
See application file for complete search history.

(56) References Cited

U.S. PATENT DOCUMENTS

| | | | | |
|---|---|---|---|---|
| 2010/0231144 | A1* | 9/2010 | Leek ........................ | H05H 9/00 315/39 |
| 2018/0082821 | A1 | 3/2018 | Ikeda et al. | |
| 2019/0314645 | A1* | 10/2019 | Ciresianu ............. | A61N 5/1082 |

FOREIGN PATENT DOCUMENTS

| | | | |
|---|---|---|---|
| JP | 5820661 | B2 | 10/2015 |
| WO | WO-2007076040 | A2 | 7/2007 |
| WO | WO-2019206969 | A1 | 10/2019 |

OTHER PUBLICATIONS

"British Application No. 2117515.3, Examination Report dated Jul. 14, 2023", (Jul. 14, 2023), 6 pgs.
"British Application No. 2117515.3, Search and Examination Report dated May 25, 2022", (May 25, 2022), 7 pgs.
"International Application No. PCT/EP2022/084282, International Search Report dated Mar. 15, 2023", (Mar. 15, 2023), 3 pgs.

* cited by examiner

RF SOURCE

PRIORITY APPLICATIONS

This application is a U.S. National Stage Filing under 35 U.S.C. § 371 from International Application No. PCT/EP2022/084282, filed on Dec. 2, 2022, and published as WO2023/099762 on Jun. 8, 2023, which claims the benefit of priority to British Application No. 2117515.3, filed on Dec. 3, 2021, the benefit of priority of each of which is hereby claimed herein, and which applications and publication are hereby incorporated herein by reference in their entireties.

This disclosure relates to an RF source and in particular to an RF source for a radiotherapy device.

BACKGROUND

Radiotherapy can be described as the use of ionising radiation to damage or destroy unhealthy cells in both humans and animals. The ionising radiation may be directed to tumours on the surface of the skin or deep inside the body. Common forms of ionising radiation include X-rays and charged particles.

A radiotherapy device typically comprises a gantry which supports a beam generation system, or other source of radiation, which is rotatable around a patient. Alternatively, static, fixed beam systems may also be used. The beam generation system is typically based on a particle accelerator such as a linear accelerator or 'linac' which comprises a radiofrequency (RF) power source, a charged particle source, and an RF cavity. Linear accelerators (especially those for medical use) accelerate charged particles such as electrons to relativistic speeds along an acceleration path through an acceleration waveguide. The acceleration waveguide comprises one or more resonant cells that surround the charged particle trajectory. The acceleration waveguide is filled with RF power from an RF power source which forms an oscillating electric field, or an electromagnetic (EM) wave, inside the cavity. Charged particles are injected from a particle source such as an electron gun into the cavity, forming a beam. As the beam traverses the oscillating EM wave, it gains energy and is thus accelerated, often up to relativistic speeds. Accelerated particles with increased effective mass deposit more energy when they collide with other matter, which is usually either biological tissue or a tungsten target, the target being used to generate X-rays. The resultant particle beam, or X-rays, may be used for imaging or treatment, so often the energy of the beam is variable.

Known linac-based radiotherapy devices perform very well, but because the RF source by necessity operates at a very high power, its operational lifetime is suboptimal. The RF source must be serviced regularly to prevent breakdown. Both servicing and breakdown of the RF source cause undesirable machine downtime.

The invention is set out in the claims. By providing first and second RF pulse generators generating pulses sequentially, operation of the system can be enhanced, the average pulse power per generator can be reduced, and the system can work in a "secondary mode" mode if one of the RF pulse generators fails.

Furthermore, by interleaving the RF pulses it is possible to provide a linac system that is driven by multiple RF source with improved stability and increased functionality in terms of running conditions that allow for energy modulation both sequentially and pulse to pulse energy variation as well as dose rate modulation.

SUMMARY

An invention is set out in the independent claims. Optional features are set out in the dependent claims.

Embodiments will now be described, by way of example, with reference to the drawings of which:

OVERVIEW

In overview, an RF source is provided comprising two or more RF pulse generators such as magnetrons which deliver RF pulses to a particle accelerator such as a linac under the control of a controller in a sequential or interleaved manner. The lifetime of the power sources is enhanced by sharing operation, providing improved life cycle costs and if one of the sources breaks the treatment can still be delivered either at a lower power, a lower frequency or both, permitting component replacement when the machine is not in use, reducing machine down time and permitting increased machine productivity.

DETAILED DESCRIPTION

Figure 1:
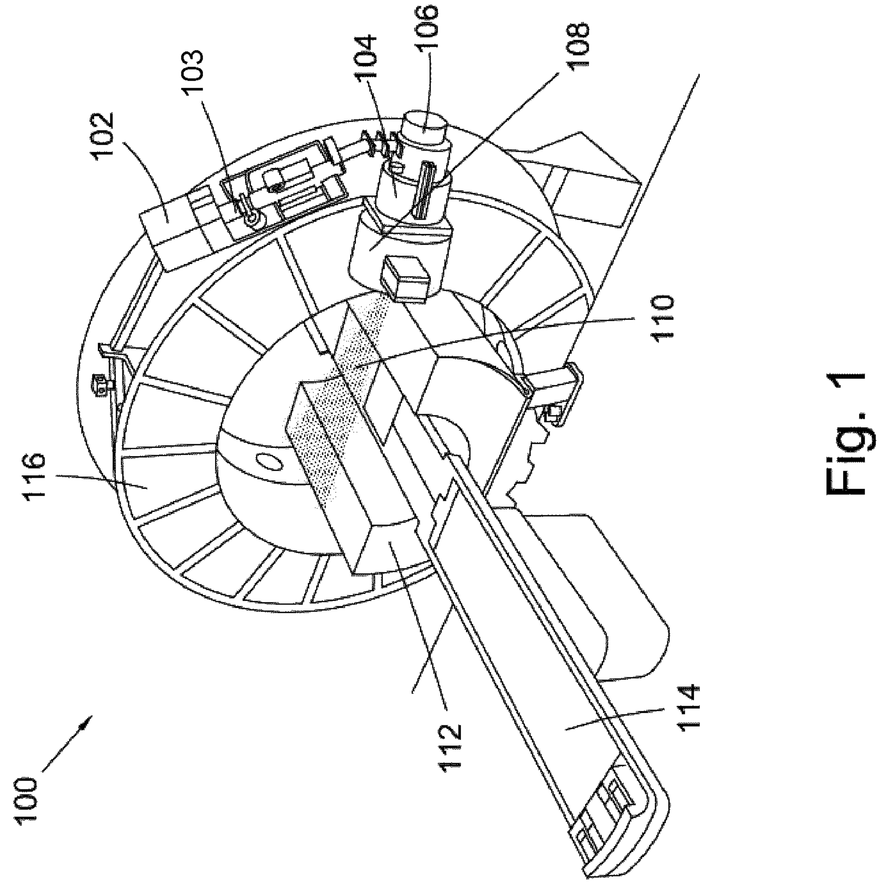
FIG. 1 shows a radiotherapy device or apparatus.

FIG. 1 shows a radiotherapy (RT) device. The device and its constituent components will be well known to the skilled person but is described here generally for the purpose of providing useful accompanying information for the present disclosure.

The device combines magnetic resonance (MR) imaging capability with a linac-based radiotherapy capability, and is known as an MR-linac device. However, the present disclosure may be implemented in any radiotherapy device, for example, a linac-based radiotherapy device without magnetic resonance imaging capability. In operation, the MR scanner produces MR images of the patient, and the RT apparatus produces and shapes a beam of radiation and directs it toward a target region within a patient's body in accordance with a radiotherapy treatment plan.

The MR-linac device 100 shown in FIG. 1 comprises an RF power source 102, an RF transmission apparatus 103, an acceleration waveguide 104, an electron source 106, a treatment head including a collimator 108 such as a multi-leaf collimator used to shape a treatment beam 110, MR imaging apparatus 112 (shown partially cut away), and a patient support surface 114. The RF transmission apparatus 103 comprises a waveguide component, which may be a copper waveguide. The depicted device does not have the usual 'housing' which would cover the MR imaging apparatus and RT apparatus in a commercial setting such as a hospital. In use, the device would also comprise the housing, part of which, together with the ring-shaped gantry, defines a bore. In particular, a part of the housing encloses the inner surface of the ring-shaped gantry, defining a bore through the device 100. The patient support surface 114 is moveable and can be used to support a patient and move them, or another subject, into the bore when an MR scan and/or when radiotherapy is to commence.

The MR imaging apparatus 112 is configured to obtain images of a subject positioned on the patient support surface 114. The MR imaging apparatus 112 may be conventional MR imaging apparatus operating in a known manner to obtain MR data, for example MR images. The skilled person will appreciate that such MR imaging apparatus 112 may comprise a primary magnet, one or more gradient coils, one or more receive coils, and an RF pulse applicator.

The RT device has a beam generation system comprising the RF power source 102, the acceleration waveguide 104, and the electron source 106. The beam generation system is configured to produce a beam of ionising radiation, otherwise known as the treatment beam 110, that is collimated and shaped by the collimator 108 and directed towards the bore. Typically, a radiation detector is positioned diametrically opposed to the collimator. The radiation detector is suitable for, and configured to, produce radiation intensity data. In particular, the radiation detector is positioned and configured to detect the intensity of radiation which has passed through the subject. The radiation detector may form part of a portal imaging system.

The beam generation system is attached to the rotatable gantry 116 so as to rotate with the gantry 116. In this way, the beam generation system is rotatable around the patient so that the treatment beam 110 can be applied from different angles around the gantry 116. In a preferred implementation, the gantry is continuously rotatable. In other words, the gantry can be rotated by 360 degrees around the patient, and in fact may continue to be rotated past 360 degrees. The gantry is ring-shaped, i.e. a ring-gantry.

The device 100 of FIG. 1 is controlled by a controller (not shown). The controller is a computer, processor, or other processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the patient support surface 114. The controller is communicatively coupled to a memory, e.g. a computer readable medium.

Figure 2:
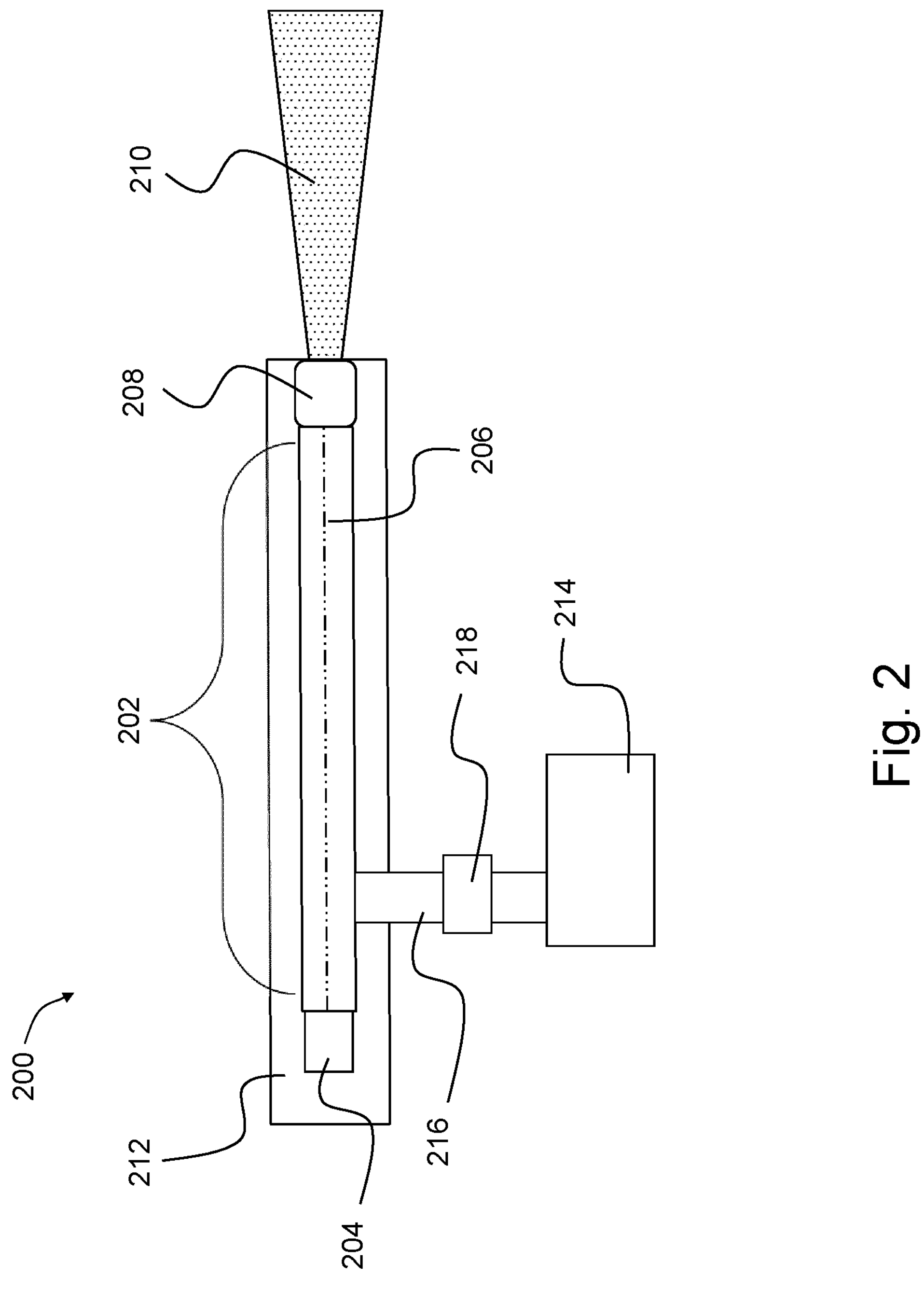
FIG. 2 shows a beam generation system for a radiotherapy device.

FIG. 2 shows an example beam generation system 200 that will be described generally for the purpose of providing useful accompanying information for the present disclosure. The beam generation system 200 is based on a linear accelerator design.

The beam generation system 200 comprises an acceleration waveguide 202 and a source 204 of electrons. The source 204 of electrons may be an electron gun, for example a triode electron gun or diode electron gun.

The acceleration waveguide 202 is configured to accelerate particles, in this case electrons, along an acceleration path 206 into a target 208, in order to produce a treatment beam 210 of radiation. The acceleration path 206 is also known as the central beam axis of the acceleration waveguide 202. The acceleration waveguide 202 comprises a series of cells. In this example, each cell has substantially the same shape and dimensions, but in other examples, that may not be so. The cells may be arranged such that each cell is RF-uncoupled/independent, and in that case each cell functions as a separate resonant cavity. In other implementations, such as the example of FIG. 2, the cells may be coupled together and, in that case, the overall coupled structure may be considered to be a single resonant cavity. In such an implementation, although the coupled cells function as a single resonant cavity, individual cells may still be referred to as cavities by those skilled in the art. The acceleration path is coincident with the centre axis of the acceleration waveguide 202 and passes through an aperture at the centre of each cell. The acceleration waveguide 202, the source 204 of electrons, the cells and the target 208 are enclosed within an evacuated and vacuum-sealed casing 212 to ensure that propagation of the electrons is not impeded as they travel toward the target 208. The vacuum-sealed casing 212 is evacuated using a vacuum system to ultra-high vacuum (UHV) conditions. As the electrons are accelerated in the acceleration waveguide 202, in some embodiments the electron beam path may be controlled by a suitable arrangement of steering magnets, or steering coils (not shown), which surround the acceleration waveguide 202. The arrangement of steering magnets may comprise, for example, two sets of quadrupole magnets.

A source of RF waves, or RF power source 214, such as a magnetron or a klystron, is configured to produce and/or amplify RF waves. The RF power source 214 is coupled to the acceleration waveguide 202 via an RF transmission apparatus 216, which usually comprises copper waveguide sections that can have a circular or rectangular cross section. A modulator is configured to pulse RF waves through the copper waveguide into the acceleration waveguide 202. Typically, the RF waves are input into a particular cell of the acceleration waveguide 202. The RF transmission apparatus 216 that connects the RF power source 214 to the input cell of the acceleration waveguide 202 may comprise a waveguide network and may contain an RF window which may separate a vacuum envelope from an SF6 envelope.

The RF transmission apparatus 216 is perpendicular to the acceleration waveguide 202 central beam axis 206 where it couples the power into the input cell. The RF input connecting pipe or tube is coupled with the acceleration waveguide 202 and joins the acceleration waveguide 202 at a substantially 90° angle. The RF transmission apparatus 216 may include a circulator 218 of any appropriate known type.

The beam generation system can operate with either a standing wave or a traveling wave configuration. In a standing wave configuration as shown, the RF power source 214 is configured to pulse RF waves into the acceleration waveguide 202, in order to set up a standing wave of varying electric field that is suitable for accelerating charged particles.

Although the RF power source 214 can operate in continuous mode, typically it operates in pulsed mode in view of the RF power levels required. An example RF wave frequency is 3 GHZ, with a pulse duration in the range of microseconds and a pulse repetition rate in the range of several hundred pulses per second. The RF power source 214 may be a commercially available magnetron such as an E2V 3.1 MW magnetron, or any standard radiotherapy magnetron, operating at 3 GHZ. Typically, the RF power source 214 produces each pulse at a particular phase in order to improve the stability of the standing wave within the acceleration waveguide 202. After it has been pulsed into the acceleration waveguide 202, some of the RF energy dissipates into the walls of the acceleration waveguide 202.

In an acceleration waveguide made up of coupled cells, the standing RF wave is established according to the resonant frequency of the coupled structure. An effect of coupling individually resonant cells together to form a single resonant cavity is that, due to dispersion, a band of different frequency oscillation modes comprising higher and lower order modes may be permitted within the acceleration waveguide 202 either side of the resonant frequency of the coupled structure. The frequency of the RF waves provided by the RF power source 214 determines the mode(s) that are excited in the acceleration waveguide 202.

There are also multiple modes of operation by which a standing wave at the resonant frequency can accelerate electrons within the acceleration waveguide. Electrons will accelerate or decelerate depending upon the polarity of the electric field they experience. The length of each cell in the cavity is designed such that the beam sees the same phase of the RF in each cell. The beam is synchronised such that on each oscillation the beam interacts with the positive part of the wave and is accelerated further.

In one operational mode, known as the zero mode, the electric field of the standing wave has the same polarity and magnitude in all cells at any given time. During the time that an electron takes to traverse a given cell and enter the next cell, the field makes a complete oscillation, for example from positive to negative and back to positive, such that the electron sees the same accelerating field it has just experienced, rather than a decelerating field. Alternatively, a 'π mode' may be used. Rather than the electric field being of the same polarity in each cell at a given time, adjacent cells have opposite polarities at a given time. However, the dimensions of each cell are such that during the time an electron takes to traverse a given cell, the adjacent cell experiences a half oscillation in field polarity such that the electron entering the adjacent cell experiences an accelerating field polarity rather than a decelerating one, and so on.

The source 204 of electrons, such as an electron gun, is also coupled to the acceleration waveguide 202 and is configured to inject electrons into the acceleration waveguide 202. The injection of electrons into the acceleration waveguide 202 is synchronised with the pulsing of the radiofrequency waves into the acceleration waveguide 202.

In some implementations, an upstream portion of an acceleration waveguide in a linac may be referred to as a buncher section. The buncher section may comprise one or more cells of the acceleration waveguide. Within the buncher section, the phase of the RF wave, whether a standing wave or traveling wave, decelerates some electrons to allow slower electrons to catch up, concentrating the electrons in bunches. The electrons are then free to move together in so called "packets" or "bunches" and the bunches quickly accelerate to relativistic speeds through the subsequent cells of the acceleration waveguide. The acceleration waveguide may be designed with a buncher section that is optimised to produce an electron beam with a particular energy and intensity by bunching electrons into a beam of short pulses.

RF waves may be input to the acceleration waveguide at a particular cell, or at more than one cell. In particular, RF waves may be input at a cell that is adjacent to the buncher portion of the acceleration waveguide. In the example of FIG. 2, the first two cells on the left-hand side of the acceleration waveguide 202 are the buncher and the following cells act to accelerate the electrons to relativistic speeds. Alternatively, the RF waves may be input into one or more of the cells belonging to the buncher section of the acceleration waveguide 202.

Once the electrons have been accelerated to faster energies, such as 8 MeV or 10 MeV, they may pass into a flight tube. The flight tube is connected to the acceleration waveguide by a connecting tube. The flight tube is also kept under vacuum conditions. This connecting tube or connecting structure is termed a drift tube. The drift tube also forms part of a vacuum tube along with the other components within the vacuum-sealed casing 212. The electrons may travel along a slalom path toward the heavy metal target. Whilst the electrons travel through the flight tube, an arrangement of focusing magnets act to direct and focus the beam on the target. The slalom path allows the overall length of the linac to be reduced while ensuring that the beam of accelerated electrons, which is comprised of electrons with a small spread of energies, is focused on the target.

The electrons travel toward the target 208 which may comprise, for example, tungsten, or another heavy metal. The impact of the electrons on the target 208 produces x-rays which form the treatment beam 210. When the electrons strike the target 208, x-rays are produced in a variety of directions. A primary collimator may block x-rays travelling in certain directions and pass only forward travelling x-rays to produce the treatment beam 210. The x-rays may be filtered and may pass through one or more ion chambers for dose measuring. The beam can be shaped in various ways by beam-shaping apparatus, for example by using the multi-leaf collimator 108, before it passes into the patient as part of radiotherapy treatment.

If a flight tube is used, the target is located inside the flight tube and is located at the end of the flight tube to seal the vacuum system. The flight tube also comprises a target window, which is transparent to x-rays, and which is positioned to allow the x-rays which are produced when the beam generation system is in operation to pass from the evacuated flight tube through the target window and into the treatment head.

In some implementations, the electrons are accelerated within an acceleration waveguide by using a travelling wave rather than a standing wave. In this case electrons travel at the phase velocity of the travelling wave, accelerated by the longitudinal electric field component. The acceleration waveguide 202 must be designed such that the phase velocity of the traveling wave does not exceed the speed of light, otherwise no acceleration of electrons will occur. In particular, using a disk-loaded waveguide, rather than a cylindrical waveguide, reduces the phase velocity appropriately such that electrons are accelerated. For an accelerator that uses a traveling wave, in addition to an RF input, the acceleration waveguide will have an RF output configured to transfer RF energy out of the acceleration waveguide and prevent it from reflecting and establishing a standing wave. If a drift tube is used adjacent to the acceleration waveguide, the RF output may be coupled to the drift tube. As with the input transmission apparatus or waveguide, which introduces RF power to the acceleration waveguide, the output waveguide through which RF power exits the waveguide can be connected via an elbow joint or 'T-shaped' joint. RF waves pass out from the evacuated system via an RF output window which seals the vacuum envelope.

Further Variations in Design

Figure 3:
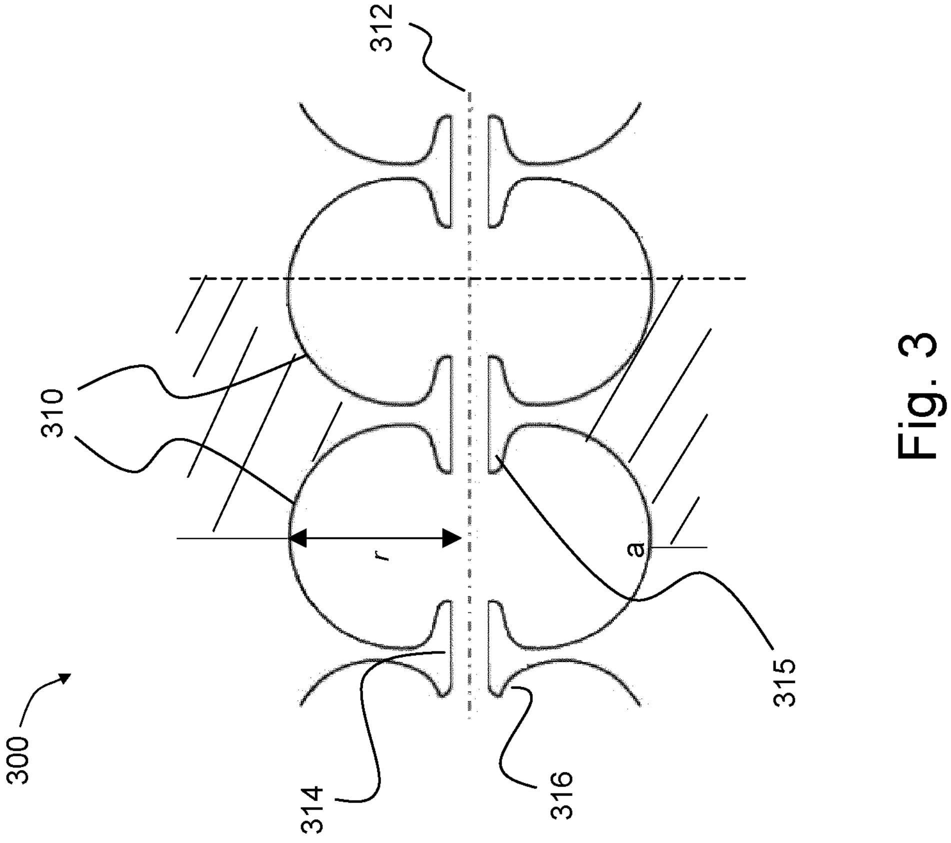
FIG. 3 shows components of an acceleration waveguide for a linear accelerator.

Referring to the apparatuses of FIG. 2 and FIG. 3, variations in design and components are possible or desirable depending upon the application requirements. For example, requirements may vary depending upon the desired type and energy of the treatment beam or depending upon the mechanical or structural design of the overall device in which the apparatus is to be used, such as the device 100 of FIG. 1.

In some implementations, the RF power source 214 may be a klystron, rather than a magnetron. Similarly, in some implementations, the RF power source 214 may be operated continuously rather than in a pulsed manner.

In some implementations, the beam generation system 200 is configured to emit either an x-ray beam or an electron particle beam. Such implementations allow the device to provide electron beam therapy, i.e. a type of external beam therapy where electrons, rather than x-rays, are directed toward the target region as the therapeutic radiation. It is possible to 'swap' between a first mode in which x-rays are emitted and a second mode in which electrons are emitted by adjusting the components of the beam generation system. In essence, it is possible to swap between the first and second mode by swapping between the heavy metal target and a so-called 'electron window'. The electron window may be made of nickel. The electron window is substantially or partially transparent to electrons and allows electrons to exit the beam generation system 200.

The beam generation system 200 also comprises several other components and systems as will be understood by the skilled person. For example, in order to ensure the linac or beam generation system does not leak radiation, appropriate shielding is also provided. The whole system is cooled by a water cooling system (not shown in the figures). The water cooling system may be used, in particular, to cool the acceleration waveguide 202, the target 208, and the RF power source 214.

A computer-based system may be used for controlling or operating various parts of the systems, devices, methods and apparatuses disclosed herein. The computer-based system can be implemented in software, firmware and/or hardware and may comprise a computer-readable medium containing instructions that, when executed by a processor, cause the system to perform any of the methods described herein.

Prior Art

Figure 4:
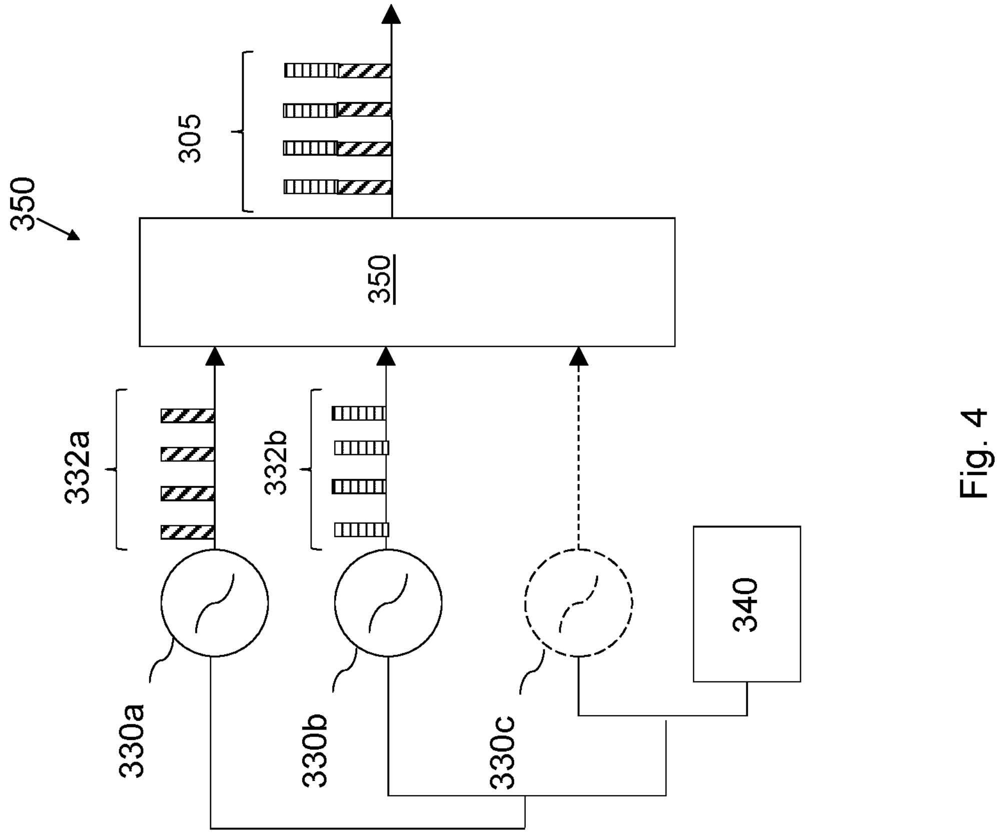
FIG. 4 shows an RF source according to the prior art.

FIG. 4 shows an RF source 350 comprising a plurality of magnetrons 330*a-c*, a controller 340 and an RF signal combiner 350. According to the prior art ('Parallel operation of magnetrons, W. Bostick et al), multiple magnetrons 330*a-c* are shown in FIG. 4. The magnetrons 3301-*c* are added to a system and run in parallel in order to generate more RF power by coherently running and matching the phase of each magnetron 332*a-b* in the system with frequency. The result of which is an additive increase in power 305 as seen in FIG. 4.

In this prior art, the magnetrons were coupled using coaxial waveguide into a terminal load and matched using an integral number of λ/2 length waveguide sections (at the fundamental frequency of the magnetron) in order that the impedance contributed by both magnetrons is the same in the system when running at the same frequency. A λ/4 mode transformer is also used in order to prevent undesirable effect on the magnetron operation (from an increase in voltage seen across the load). This combination of the RF pulses from the magnetrons is represented by item 350 via this mechanism in FIG. 4.

The system in this prior art could be adapted to N successive magnetrons as was shown by adjusting the loads (matching) and path lengths accordingly so that phase of each of the magnetrons is equal at the loads there would be good impedance matching when all the magnetrons are run on frequency, although this is a far more complicated system and a far more complicated analysis via a circuit model is required to ensure this matching.

The advantage of such a system if it were to be used in conjunction with a medical linac system is that it would offer the possibility of either increased dose rate or increasing the energy provided by the linac. In order to increase the dose, both magnetrons would be run concurrently as in FIG. 4 this would increase the RF field inside the linac the electron gun (or particle source) would then be run at a higher beam current until the beam loading in the linac produces the same energy output as previously. In order to run the linac at a higher energy range the electron gun would not be appreciably adjusted keeping the beam current the same the resulting higher field in the linac would result in a higher beam energy in the relativistic section. We note that some adjustment in beam current would be necessary in order to maintain the bunching region of the linac under the new power conditions.

The present invention is directed towards the benefits of both interleaving the RF pulses produced from multiple magnetrons on a medical linac system which allows for different treatment modalities to be realised. It also noted that the reliability and service aspect that a multiple magnetron system would offer which is something that is not considered in prior art (see 'Parallel operation of magnetrons, W. Bostick et al).

An Improved FR Source

Figure 5:
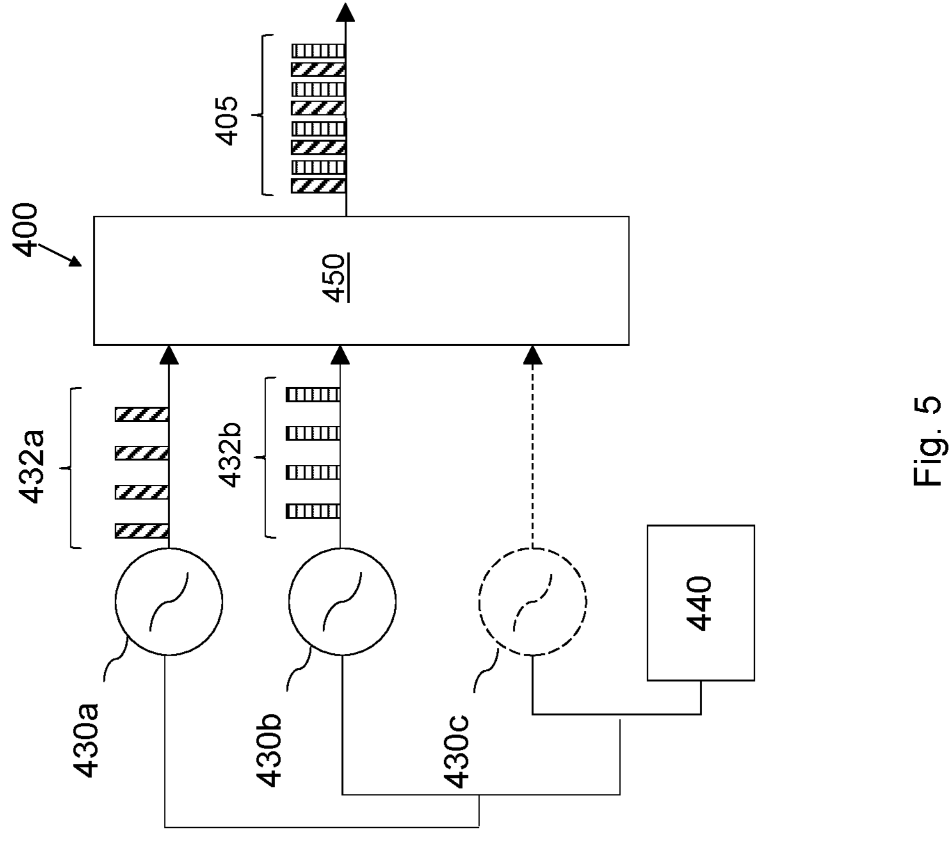
FIG. 5 shows an RF source according to the present invention.

Turning in more detail to the invention described herein, FIG. 5 is a schematic depiction of a plurality of RF pulse generators or power sources such as magnetrons 430*a-c* configured to provide RF pulses to a radio therapy device. Specifically, the magnetrons are configured to provide pulses to a resonant cavity/electron accelerating waveguide of a radio therapy device of the linear accelerator in the manner described above. FIG. 5 shows an RF source 400 comprising a plurality of magnetrons 430*a-c*, a controller 440 and an RF signal combiner or interleaver 450.

The plurality of magnetrons 430*a-c* comprises at least two magnetrons and optionally further magnetrons as well, each configured to provide RF power in the form of respective pulse signals 432*a, b* . . . at respective pulse repetition rates. The pulses are temporally interleaved, that is, they are generated successively from each magnetron and then repeated. It will be seen therefore that for N magnetrons, and a combined output pulse rate of M pulses per second, each magnetron will generate M/N pulses per second, in staggered or sequential order.

The interleaver 450 is configured to receive the RF signals 432 sequentially from N successive magnetrons as input pulses and interleave them in order to produce an interleaved signal 405 comprising a stream of output pulses at a higher pulse repetition rate M comprising the sum of the individual rates from each of the magnetrons. Of course, alternative pulse ordering schemes can be contemplated for example increasing the pulse rate or number generated by recently added or refurbished magnetrons under control of the controller 440, and varying pulse repetition patterns per magnetron accordingly.

It is also possible that with the addition of another tank/pusler unit on a modulator (based on space and available power) that more than one RF source could be run rather than having to add further additional hardware to the infrastructure of the linac gantry other than the additional N successive RF power sources 430*a-c* (FIG. 5), supporting structures on the gantry, the interleaver 450 and modifications to the control system.

The interleaver may be any device able to combine multiple RF such as a standard waveguide Combiner (of which there are multiple configurations ranging from Y structures or combinations of Y structures), a Magic T junction, Power splitter (effectively a variant of a combiner but run in reverse). All of which are considered standard RF waveguide components. The coupling of the magnetron need not be restricted to purely standard rectangular waveguides, but may be any waveguide type such as circular or coaxial or that described in the prior art.

The power and pulse repetition rate per magnetron can be varied in a range of manners. In one approach, the power and pulse repetition rate can be provided at full operational levels if necessary.

In preferred embodiments, the magnetrons are automatically frequency controlled (AFC) to ensure that they are optimally tuned to the linac desired operational frequency hence enhancing cavity stability and performance. This can be performed by controller 440 in any appropriate manner; additionally, the AFC can be controlled by a common controller or individually per magnetron as appropriate. Similarly, to enhance operational performance, phase locking can be implemented between consecutive pulses to enhance linac cavity stability and operational lifetime.

Operation and "Secondary Mode" Mode

In operation, the RF source can be driven by the controller 440 such that each magnetron is pulsed sequentially, implementing automatic frequency control and phase lock. The pulse repetition rate, or repetition pattern per magnetron can be controlled by the controller and varied according to operational requirement. Similarly, the pulse energy per magnetron can be controlled per controller either to provide multiple energy modes between consecutive pulses, or to provide secondary mode operation or compensation.

Figure 6:
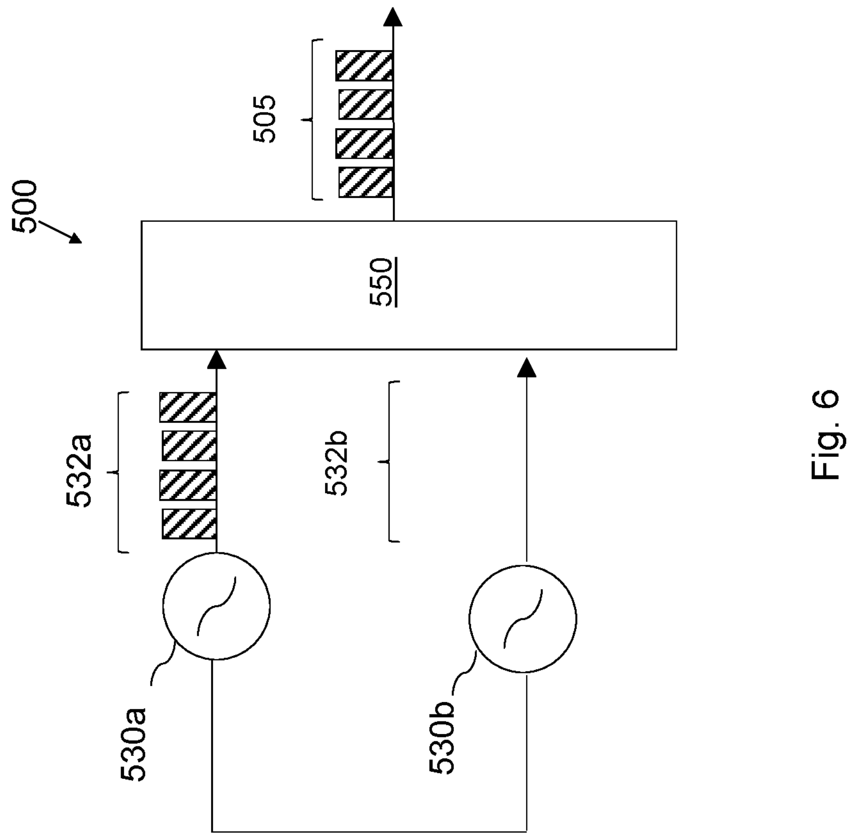
FIG. 6 shows an RF source according to the present invention in "secondary mode" mode.
Figure 7:
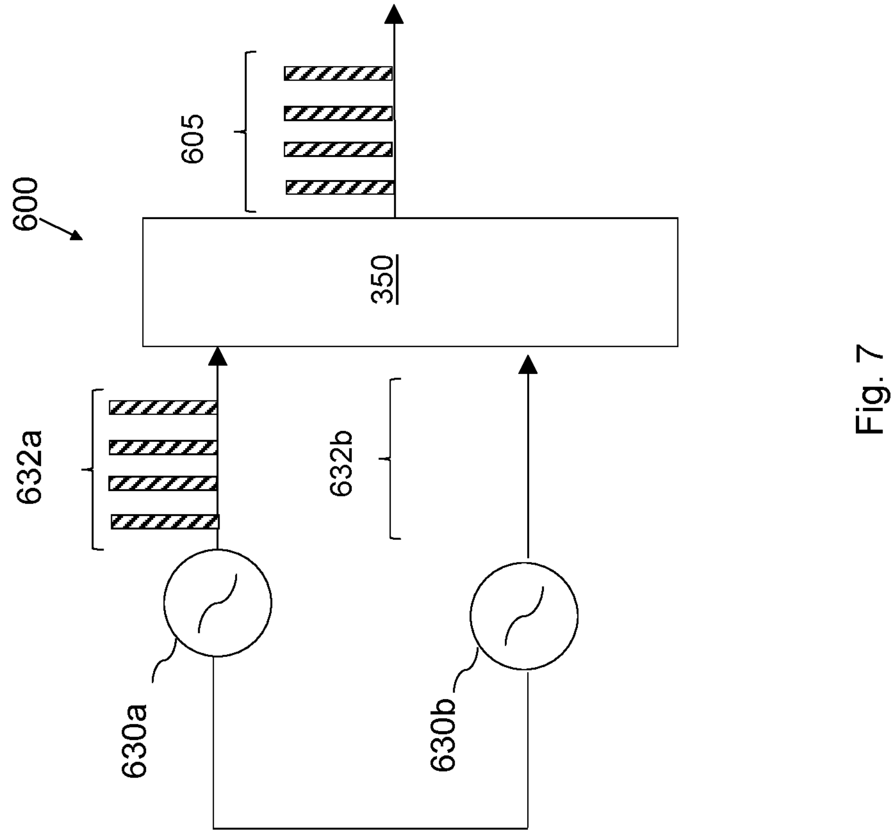
FIG. 7 shows an RF source according to the present invention in "secondary mode" mode.

In order to provide a service oriented "secondary mode" mode, the controller can be configured to detect individual magnetron failure and revise operation of the remaining magnetrons accordingly. For example, in a case of a dual magnetron arrangement, if one magnetron is detected to fail, the controller can change the pulse repetition rate of the operational magnetron for example doubling it to the desired pervious combined pulse repetition rate and/or increase the pulse power generated per pulse. FIG. 6 is used as an illustrative example for a dual magnetron system in which the second magnetron 530*b* has failed, here the pulse repletion rate on magnetron 530*a* is increased in order to compensate for the failed magnetron allowing the system to provide the same performance as in FIG. B if this was how the system was being operated beforehand. FIG. 7 is used as an illustrative example for a dual magnetron system in which the second magnetron 630*b* has failed, here the peak pulse power on magnetron 630*a* is increased in order to compensate for the failed magnetron allowing the system to provide the same performance as in FIG. 4 if this was how the system was being operated.

In the case that the frequency is doubled, and full pulse power is provided then it will be seen that operation will continue seamlessly and can be maintained until the other, failed magnetron can be serviced or replaced. In the case of greater numbers of magnetrons, the pulse energy, repetition rate or pattern can again be modified appropriately. Alternatively, to conserve the remaining magnetron(s) operation can continue at the original individual pulse energy and/or repetition rate with performance modified accordingly. Therefore, the present invention provides the technical benefit of improved redundancy and error compensation.

Components

The nature of the various components described herein will be well known to the skilled reader but for purposes of completeness, the RF source may be an E2V3.1MW magnetron or any standard radio therapy magnetron for example operating at 3 GHZ. Alternatively, the RF sources can be any other appropriate source of RF pulses such as Klystrons. Automatic frequency controllers for magnetrons are well known and any appropriate type can be used for example a feedback controlled mechanical tuner for the or each magnetron cavity. Any other appropriate type of AFC can be used for example injection locking or reflection systems as appropriate. Any appropriate phase locking approach can similarly be adopted for example using injection locking; it will be noted that use of injection locking permits both AFC and phase locking simultaneously. Control of the magnetrons can be through any appropriate software or hardware base control system, interoperating with other components of the system as a whole for example control of the injection gun for synchronisation of pulses. The interleaver may be any appropriate type of combiner such as a magic tee or other hybrid combiner such as a 3 dB combiner.

Benefits of the Invention

It will be seen that by virtue of the claimed configuration, increased lifetime, reduced maintenance and enhanced power control variation can be provided according to the claimed approach. Yet further, by phase locking and AFC interleaving the magnetrons the lifetime of the power sources can be further improved providing improved life cycle costs.

In a conventional medical radiotherapy system a single power source (such as a magnetron or a klystron) is employed and due to the demanding requirements for the maximum desired dose rate from the system this power source as the single point of failure (as previously mentioned in the "secondary mode" mitigation proposal).

According to a different implementation aimed at service improvement of the medical device would be consider running the device with the output of both magnetrons reduced but interleaved using either method depicted in FIG. 4 or 5. The aim of which would be to provide a system run by two or more magnetrons that would equivalent to a system run with a single magnetron run at full power. As the life time of a magnetron is determined largely in part to the number of hours of running at a given pulse repetition rate, the overall lifetime of the system would therefore be greatly improved by running the system using either method depicted in FIG. 4 or 5 rather than that depicted in the equivalent single magnetron systems (e.g. as demonstrated in FIGS. 8 and 9).

There are further inherent limitations to a system run via a single magnetron, that are mitigated by the proposed invention. The first of these is that any pulsed magnetron is limited to the maximum pulse width that can be produced, by interleaving the pulses it will be possible to extend the width of the RF pulse injected into the linac as demonstrated in FIG. 5, where the combination of interleaved pulses 432*a* to *b* when frequency locked and pulsed with a delayed (overlapping) sequence would produce a much longer RF pulse than could be obtain than that produced from a single magnetron. The second limitation is the maximum pulse power that a single magnetron can produce, but by both frequency and phase locking multiple magnetrons it is possible to increase the overall pulse power injected into the linac as demonstrated in FIG. 4, where the combination pf pulses 332*a*-*b* are constructively added to produce a larger amount of RF pulse peak power than that a single magnetron could produce.

The term interleaving is used herein to refer to how the pulses from additional RF sources are added to that of the first RF power source. Traditionally this has been used to effectively add the pulses together by matching the frequency and locking the phase (see FIG. 4). What is being proposed here is to offset the pulses when they are added together in terms of either slightly adjusting the phase, dropping pulses, or altering the PRF of the additional RF power sources to provide a range of different treatment modalities.

Figure 10:
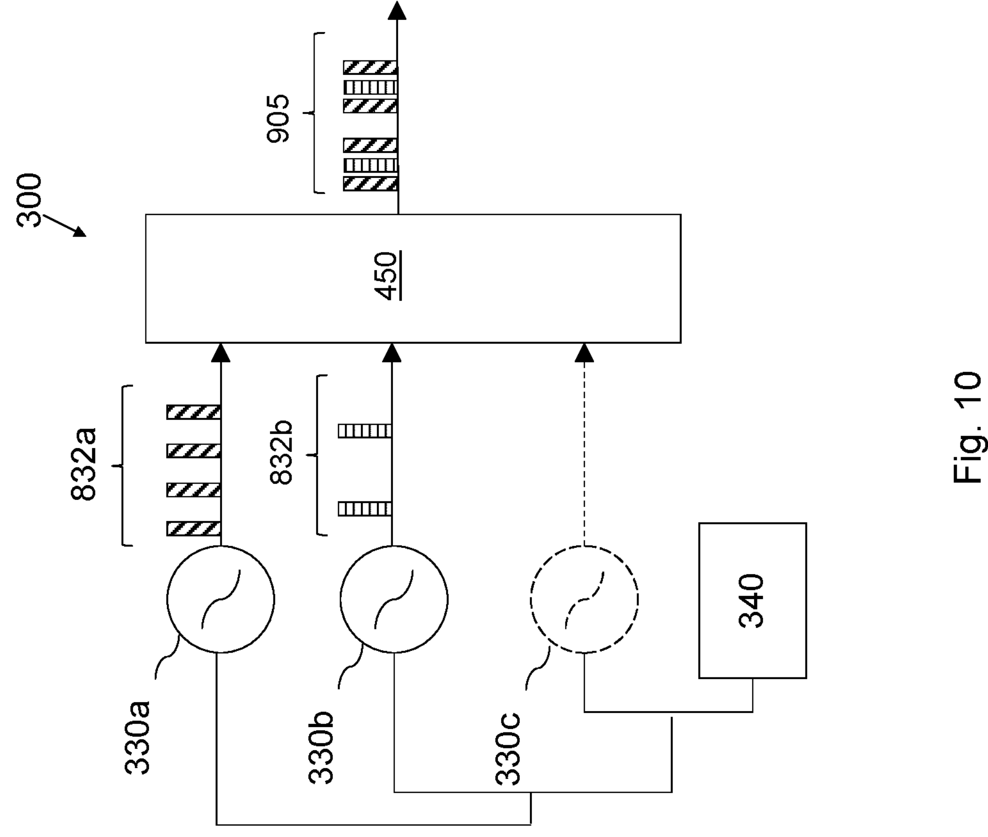
FIGS. 10 and 11 show example RF sources with dual magnetron systems.
Figure 11:
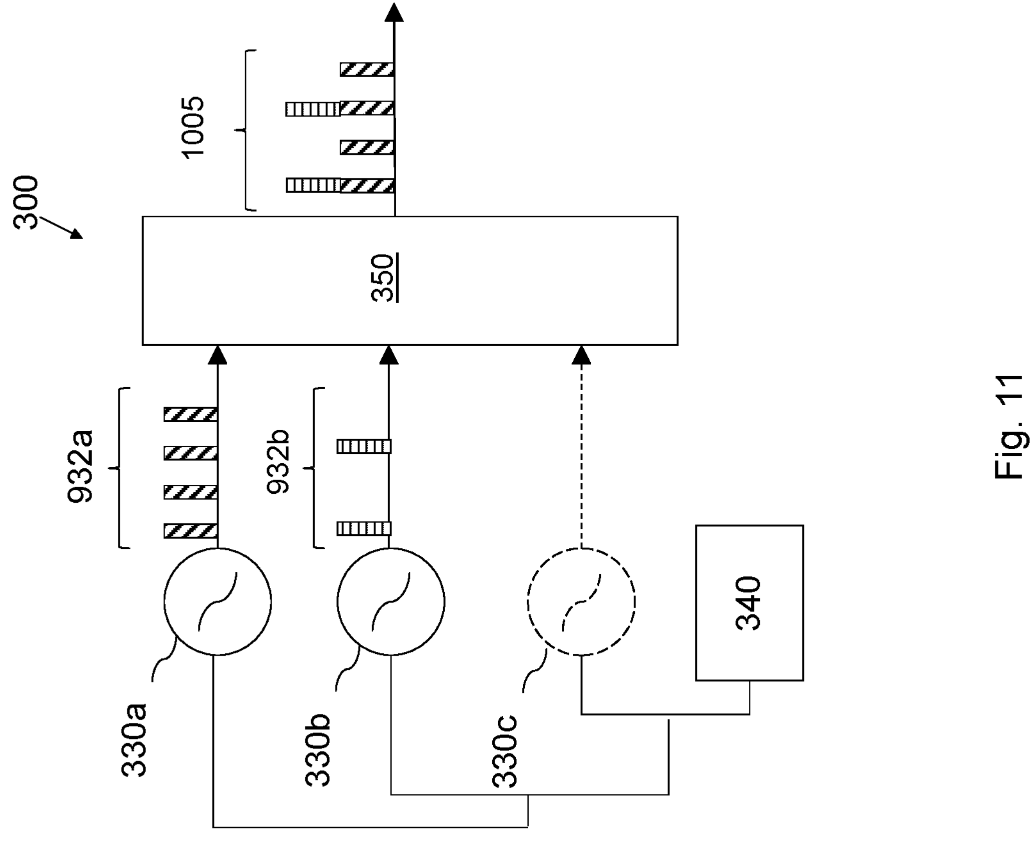

A further limitation to a system run via a single magnetron is with respect to the stability limitation of a magnetron due to the imposed magnetic field (be it a permanent or an electromagnet) as the pulse power settings are altered on the magnetron. In practice this stability, seen in terms of the dose rate supplied by the linac, is in the order of the 10 ms range. If the power conditions of a magnetron are changed faster than this, then this affects the stability of the overall system as the static interaction of the pulse to pulse generated from the magnetron is no longer stable. If instead a dual magnetron system is used as an illustrative example as seen in FIG. 10 then it is possible to control this power condition stability by keeping one magnetron 832*a* running under fixed operating conditions and varying or adding the pulse width via altering the PRF of the other magnetron 832*b* which would produce a more stable overall interleaved RF pulse 905 than would be achieved by constantly ramping a single magnetron up and down in operating conditions additionally offering quicker treatment modalities. There are many combinations of such operation that are possible using such a configuration including that of varying the peak power provided per pulse as shown in FIG. 11 as an illustrative example. Static treatment modes of the aforementioned pulsing conditions where both magnetrons are run to set conditions for a treatment regime such as that in FIGS. 10 and 11 rather than ramping the PRF condition on a given magnetron during a treatment.

Pulse 'dropping' on either of the magnetrons is also possible. 'Dropping' allows a simultaneous multiple energy system, however such an operation would negate the obvious benefit of magnetron stability previously discussed as this represents a change in the pulse power conditions of either of the magnetrons. It is more beneficial to drop the pulse on the particle source (for example the electron gun) rather than the magnetron itself. Pulse 'dropping' is simply missing out some of these RF pulses for example one may wish to miss out every third pulse from the system or any combination of pulses.

In any of the above operating conditions (one to three) to mitigate the single magnetron limitations it is of course possible to extend this to a multiple N number of interleaved magnetron.

Use in a Radiotherapy Device

The embodiment of the output from the interleaved multiple magnetrons is intended for the use in a radiotherapy device in the invention described herein. It is a well-known problem that a limiting factor in radiotherapy device design is the space the device takes up.

This invention can be used for either a travelling waveguide system (TWG) or a standing waveguide system (SWG) and is not limited to a specific linac design, as such it can be considered as a retro fixable feature to an existing radiotherapy system limited to the space claim and control system that already exists.

Figure 9:
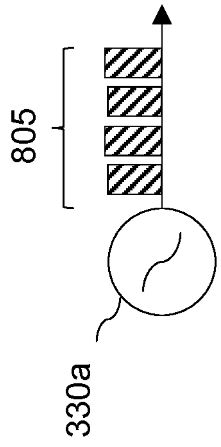
FIGS. 8 and 9 show RF source with single magnetron systems.
Figure 9:
Figure 8:
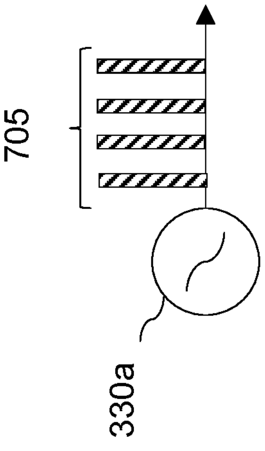
Figure 12:
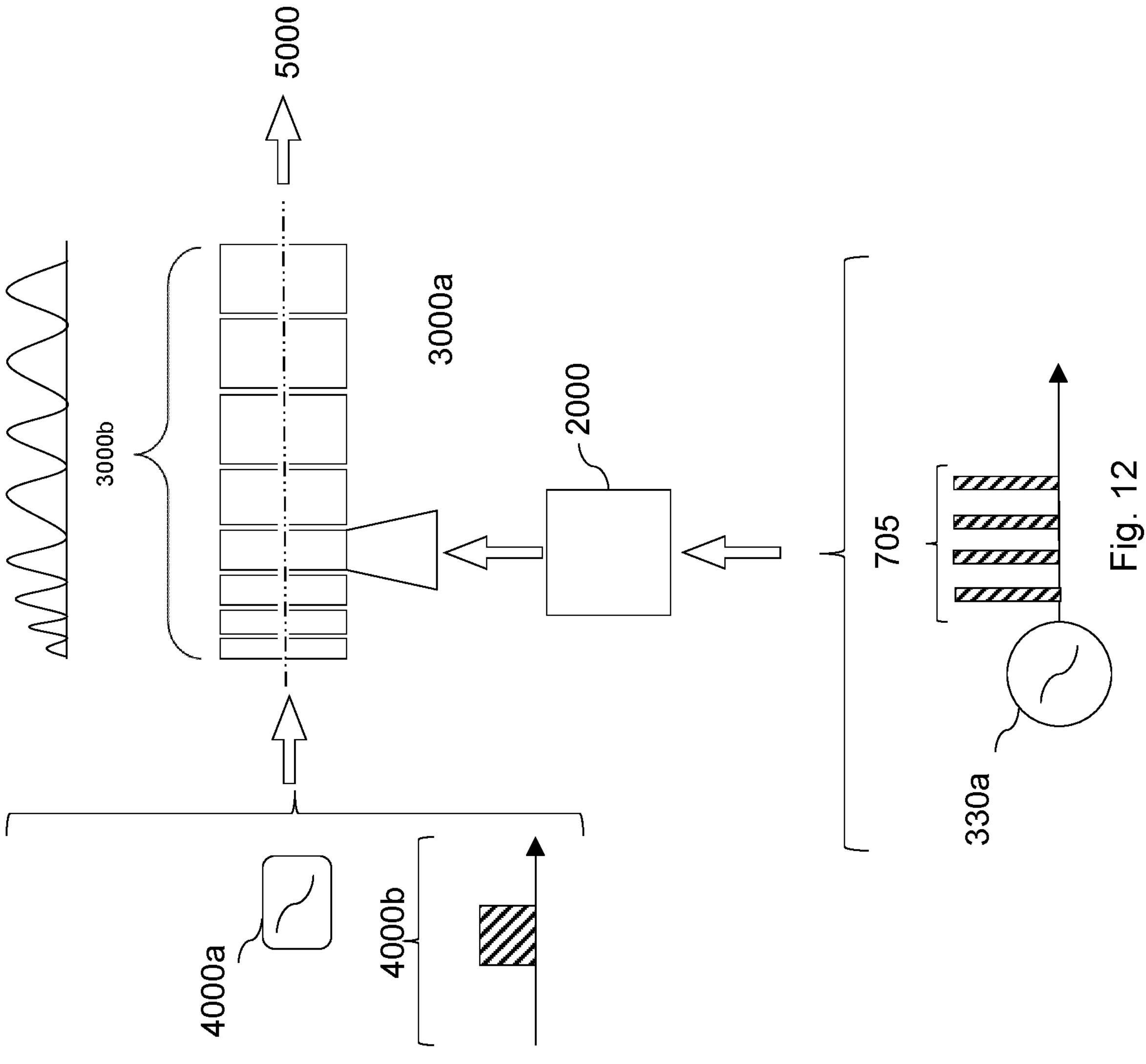
FIG. 12 shows a single magnetron RF source as part of a radiotherapy device.

FIG. 12 shows a conventionally run radiotherapy machine using a single RF input (as previously described using FIGS. 8 and 9. In this typical configuration the RF power supply 2000 is protected from any detrimental effects of reverse power by means of either a circulator or and isolator. The accelerating field 3000*b* is produced from the injected RF power inside the linac 3000*a*. The particle beam 4000*a* that is accelerated inside the linac is generated by a particle source 4000*b* (which for example may be an electron gun), the particle source introduces an initial beam current into the linac.

This beam is bunched and then accelerated by the linac producing an output dose rate at a given energy all dependent on the operating and running conditions of the system 5000.

There are several separate and distinct ways that energy variation may be achieved in either a TWG or SWG linac.

Figure 13:
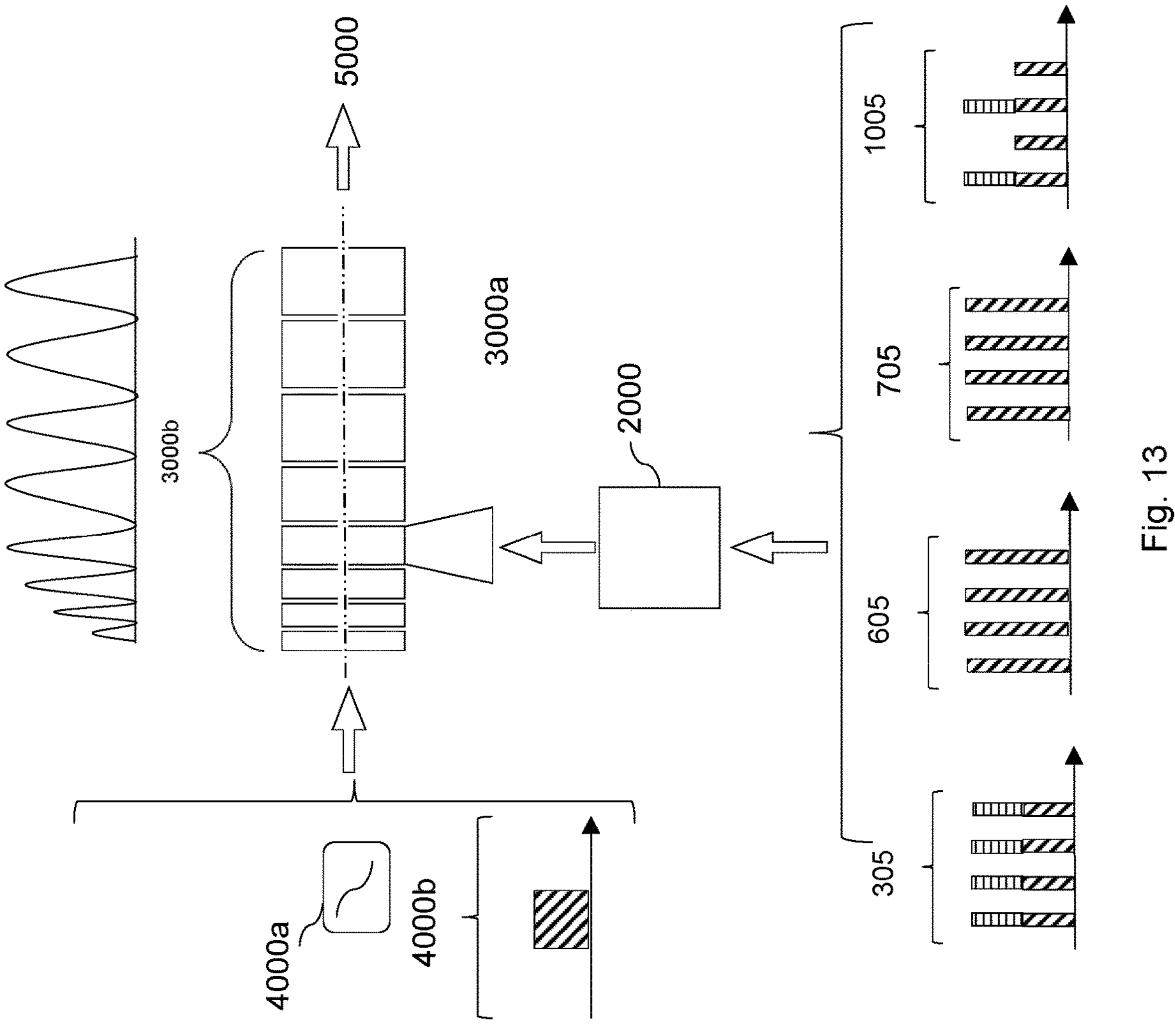
FIGS. 13 to 17 show example RF sources as part of a radiotherapy device.

In a first example method, the electric field is raised within the linac structure by increasing the peak RF pulse power at the resonant frequency of the linac whist maintaining the same beam current from the particle source (often an electron source). In this scenario as the beam loading is effectively the same the resulting output beam current at the target will be the same only accelerated with a higher energy. This operation is represented by FIG. 13 in which any of the outputs 305, 605, 705 or 1005 previously discussed from FIGS. 4, 7, 8 and 11) can be used to achieve this using the previously described running conditions of interleaving the RF sources. Running the system with the input 1005 is preferable because more than one energy can be derived pulse to pulse and as has already been discussed this would offer greater stability than a single sourced RF system.

Figure 14:
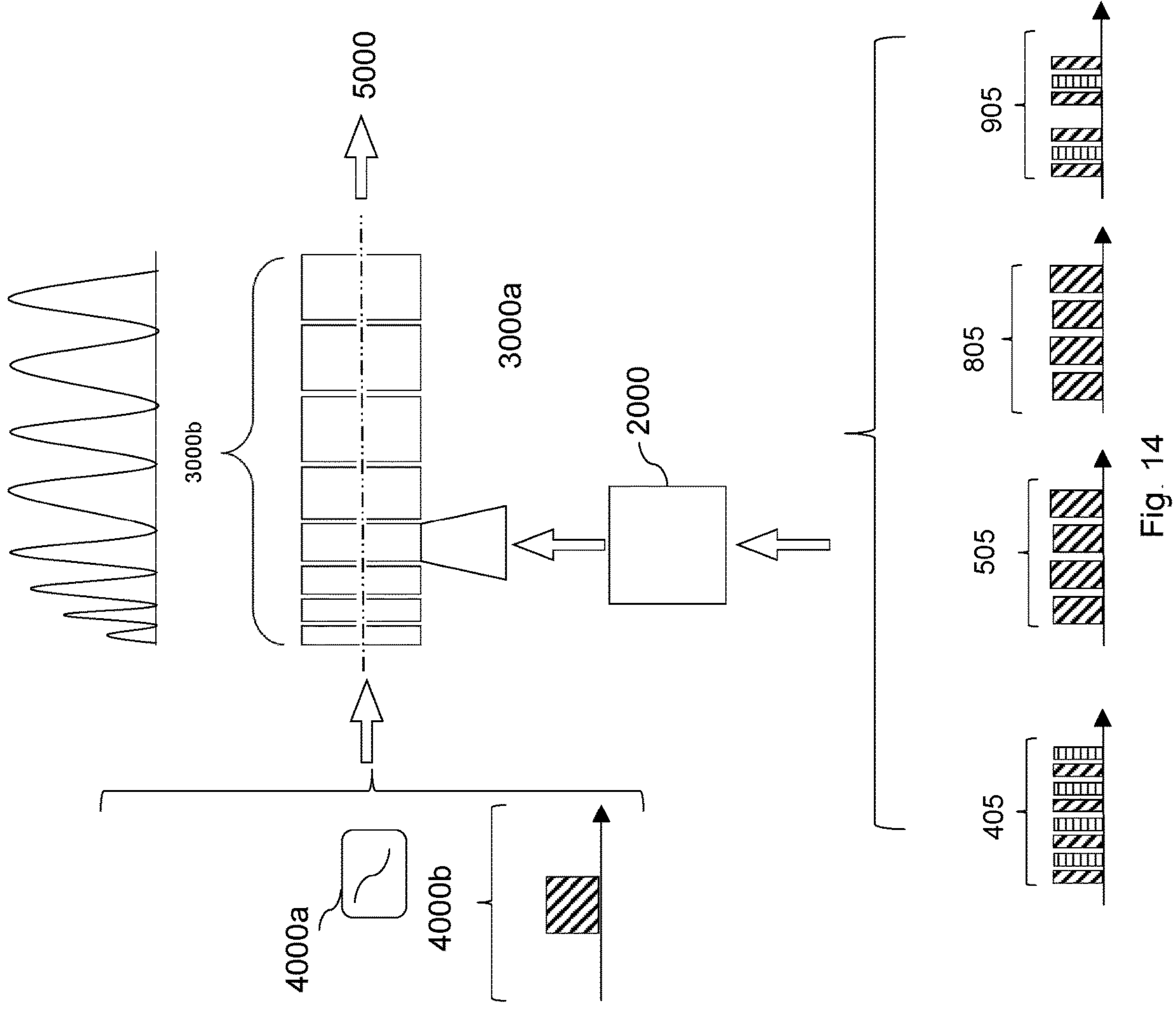

In a second example method, the pulse width of the RF pulse is altered whist maintaining the same beam current from the electron gun to obtain a sub optimal system which is either under-beamloaded so that the energy of the particles reaching the target will be at a higher energy but lower dose rate. Or in the case where the system is run sub optimally in an over-beamloaded condition such that the dose rate is higher but the beam reaching the target is of a higher energy. This is represented in FIG. 14 in which any of the outputs 405, 505, 805 or 905 taken from FIGS. 5, 6, 9 and 11 can be used to achieve this along with altering the PRF of the RF sources to achieve the sub optimal conditions. Again, running the system with the input 1005 is preferable because more than one energy can be derived pulse to pulse and as has already been discussed this would offer greater stability than a single sourced RF system.

Figure 15:
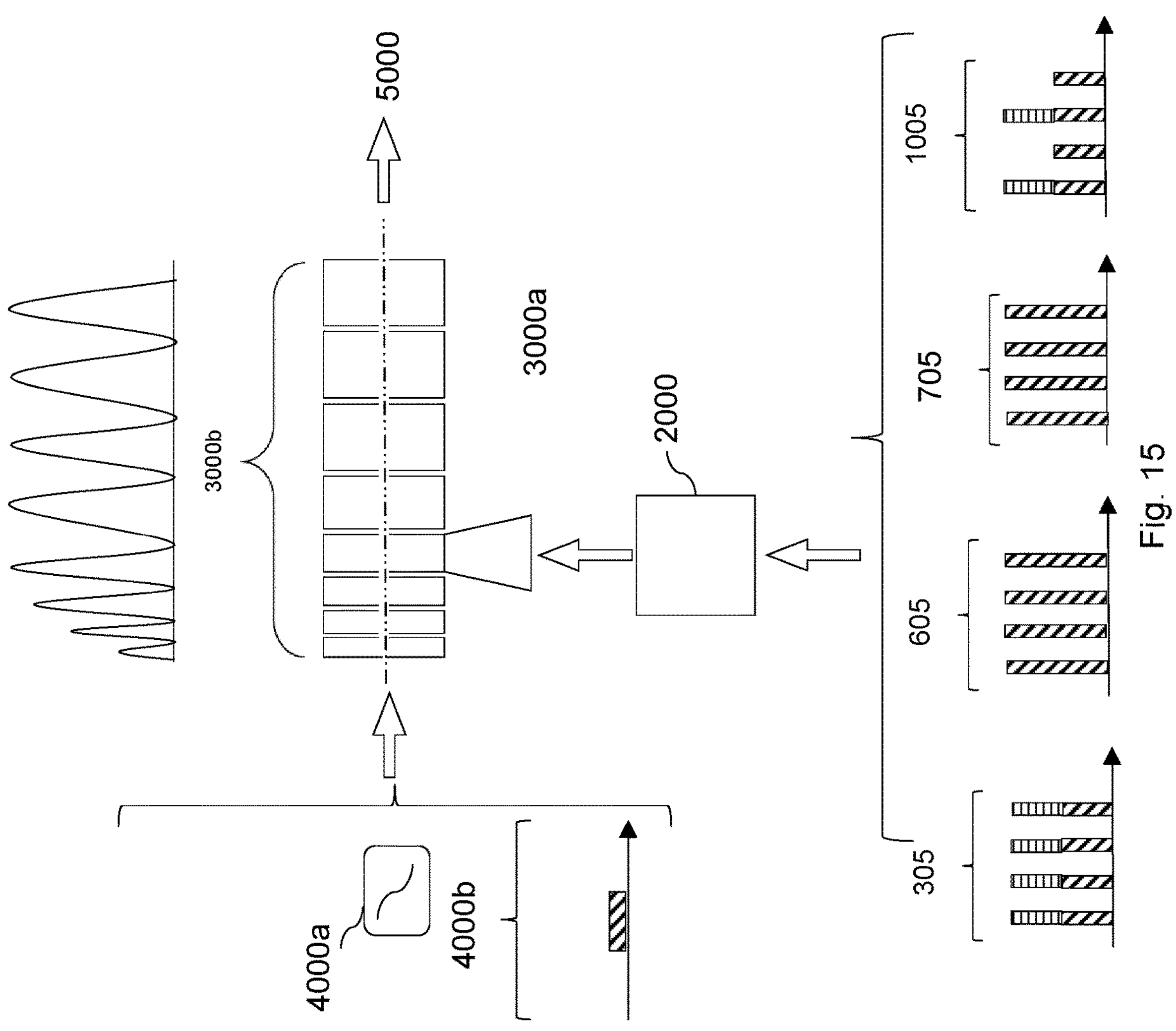

In a third example method, the pulse width is maintained but the beam current injected into the linac from the electron gun is varied, this is analogous to the second method for energy variation in that it results in a sub optimal system that is reliant on the beam loading effect for energy variation. This is represented by FIG. 15 in which as an example inputs 305, 605, 705 or 1005 (taken from FIGS. 4, 7, 8 and 11) are used as example inputs (where the pulse width is maintained) but the injected beam current item 4000*b* is varied to obtain a sub optimal system via the beam loading effect.

Additionally, analogous to the aforementioned discussed methods of energy variation of a linac system (either TWG or SWG) there are several distinct ways in which dose rate variation may be achieved these are linked to second and third methods used in the energy variation methods described above in terms of the beam loading effect within the linac previously described.

It will be appreciated that the RF source can be used in any appropriate apparatus for example a radio therapy apparatus for generating electron pulses in a linac to generate x-rays for a Tungsten target or for direct therapeutic use as appropriate.

Modifying Dose Rate

The dose rate is a very important feature for a medical linac device and for a given treatment energy it is often desired to be as high as possible. The following methods describe how the dose rate can be modified to be as high as possible.

Figure 16:
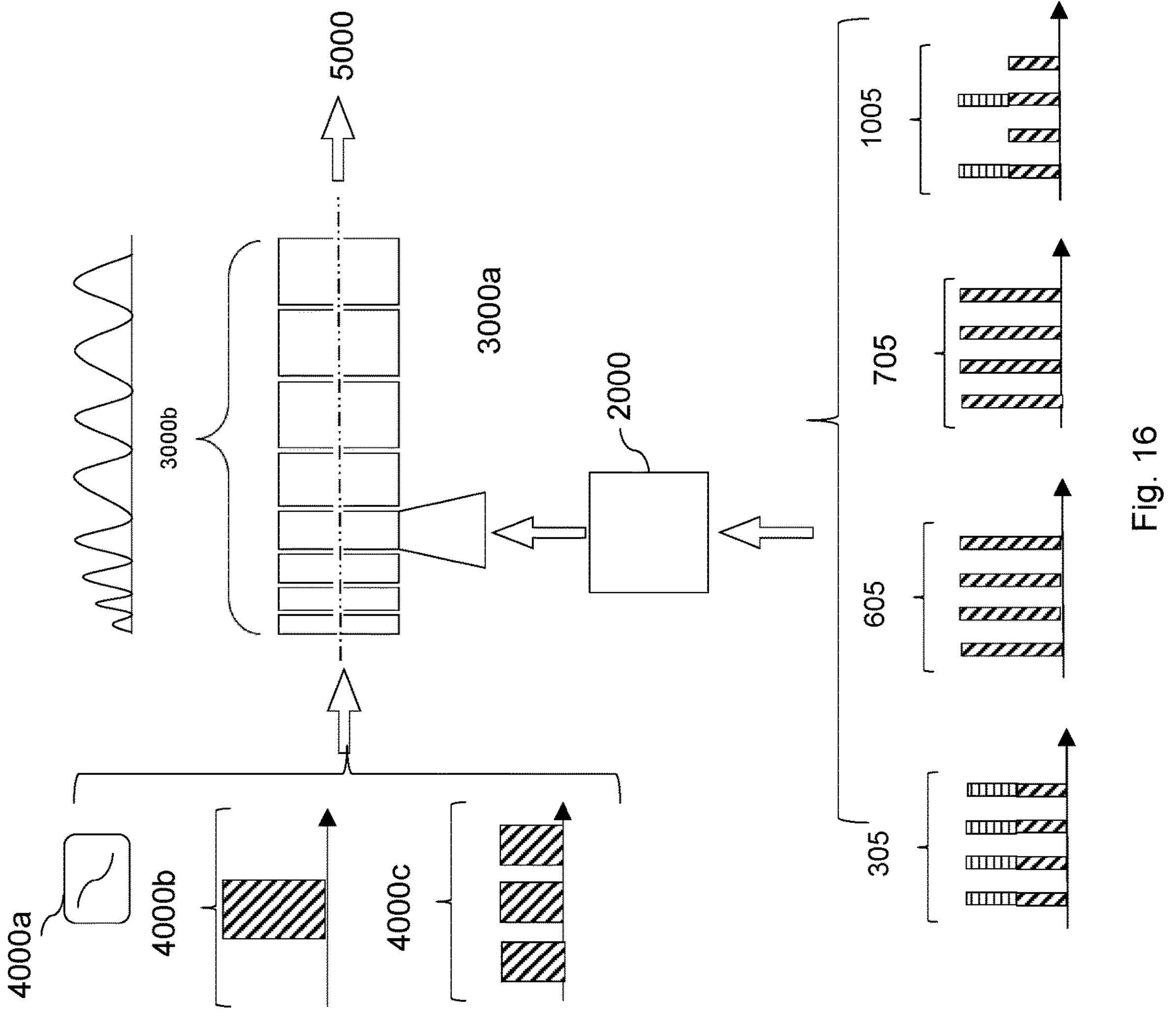

According to a first method, the accelerating field is increased inside the linac by raising the peak power per pulse and then over beam load using the electron gun to drop the energy back down to the previous treatment level, the next result is an increased dose rate at the treatment energy. The particle source can be adjusted to increase the beam current by increasing the total amount of beam current per pulse represented by item 4000*b* in FIG. 16, or by increasing the pulse repetition rate of the particle source as represented by item 4000*c* in FIG. 16. The result of either method will be an increase in the overall beam current within the linac leading to over beam loading and reducing the field inside the linac back to the same level as the original treatment level as represented by item 3000*b*. This is represented by FIG. 16. in which as an example inputs 305, 605, 705 or 1005 (taken from FIGS. 4, 7, 8, 11) are used as example inputs (where the pulse width is maintained) but the injected beam current item 4000*b* or 4000*c* is varied to obtain a sub optimal system via the beam loading effect as described.

Figure 17:
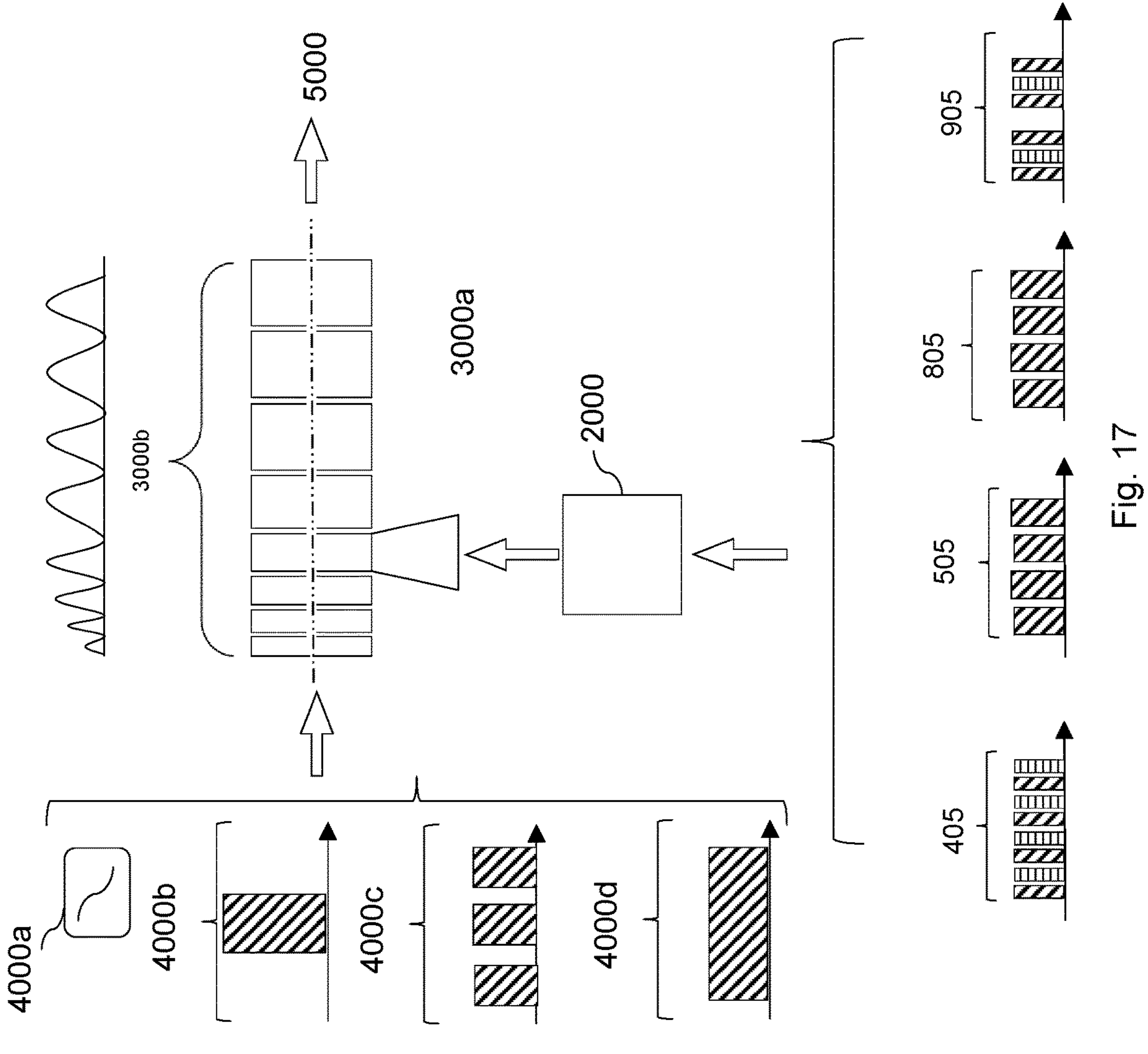

According to a second method, the accelerating field is increased inside the linac by increasing the pulse length per pulse and then over beam load using an increased pulse length on the particle source (which is often an electron source) to drop the energy back down to the previous treatment level, the next result is an increased dose rate at the treatment energy. The increased RF pulse length allows for the extension of the beamloading under these conditions by the particle source, that would otherwise not be possible on a conventional radiotherapy system. The particle source can be adjusted to increase the beam current offered by the increased RF pulse width (see FIG. 17) by increasing the total amount of beam current per pulse represented by item 4000*b*, or by increasing the pulse repetition rate of the particle source as represented by item 4000*c*, or by the increased RF pulse width by also increasing its pulse with by item 4000*d*. The result of any of the methods will be an increase in the overall beam current within the linac leading to over beam loading and reducing the field inside the linac back to the same level as the original treatment level as represented by item 3000*b*. This is represented by FIG. 17. in which as an example inputs 405, 505, 805 or 905 (taken from FIGS. 5, 6, 9 and 11) are used as example inputs (where the pulse width is varied) but the injected beam current item 4000*b*, 4000*c* or 4000*d* is varied to obtain a sub optimal system via the beam loading effect as described.

Static Multi-Energy Beam

While conventional medical linacs are typically only capable of producing a single beam energy per treatment fraction, systems and methods disclosed herein (such as the examples of FIGS. 10, 11, and 13-17) may be used to operate a radiotherapy linac in a multi-energy mode. By adjusting the electron beam energy within the linear accelerator on a pulse to pulse basis by using the approaches described above, a three-dimensional static treatment is enabled. Varying the electron beam energy alters the effective treatment depth of the radiotherapy treatment beam. Combining that capability with cross-sectional beam shaping technology provides a three-dimensional dose shaping capability. Furthermore, using gantry rotation during treatment can introduce a further, angular dimension and thus extend the capability to a four-dimensional dose delivery capability. Furthermore, said capability is achievable within a single radiotherapy treatment fraction, unlike current approaches in which the beam energy is fixed per fraction and is varied across different fractions.

Accordingly, a method of operating an RF source for a radiotherapy device comprising first and second RF pulse generators arranged to deliver RF pulses to a particle accelerator is disclosed herein. The RF pulse generators may be arranged as described as in the examples of FIGS. 10, 11, and 13-17. In some examples, more than two RF pulse generators may be used. The method may be performed in the systems disclosed herein.

At a first step, the method comprises controlling the first and second RF pulse generators to generate a series of interleaved pulses. Each of the first and second RF pulse generators is arranged to generate a series of pulses, which are then interleaved such as by using an interleaver as disclosed herein.

At a second step, the method comprises delivering the series of interleaved pulses to the particle accelerator of a radiotherapy device, such as that of the linac-based devices and systems described herein. Each of the first and second RF power sources is arranged to generate pulses at a different respective power.

By interleaving two or more RF sources of different pulse powers and combining that with varying the input particle injection into the accelerating structure, it is possible to run a linac in a multi-energy mode, where the energy configuration is determined by the combination of the number of attached interleaved RF power sources. In some examples the two or more RF sources are phase-locked with each other.

In some examples, the pulses are interleaved such that the duty cycle of pulses from the first and second RF pulse generators is 50%. However, the duty cycle of the interleaved pulses from the first and second RF pulse generators need not be 50%, and in other examples, the duty cycle may be any percentage within the percentage range from 0 to 100% for either of the first or the second RF pulse generators.

The first and second RF pulse generators are set at different power levels to obtain a change in treatment beam energy (which corresponds to a depth of maximum build up within the body), which would naturally result in a small frequency difference between the respective running/set conditions of the first and second RF pulse generators.

In some examples, the method further comprises varying an electron input of the particle accelerator during a radiotherapy treatment fraction session.

In some examples, the method further comprises using the RF source to generate a radiotherapy treatment beam and rotating the radiotherapy treatment beam about a patient. The radiotherapy treatment beam may be rotated about the patient using a gantry-based system as described herein.

The invention claimed is:

1. An RF source for a radiotherapy device, comprising:
a first RF pulse generator;
a second RF pulse generator wherein the first RF pulse generator and the second RF pulse generator are arranged to deliver RF pulses to a particle accelerator; and
a controller arranged to:
control the first RF pulse generator and the second RF pulse generator to generate pulses sequentially;
control the first RF pulse generator to generate pulses under one or more fixed operating conditions; and
alter a pulse-repetition frequency of the second RF pulse generator.

2. The RF source as claimed in claim 1, wherein the first RF pulse generator and the second RF pulse generator comprise magnetrons.

3. The RF source as claimed in claim 1, wherein the controller includes automatic frequency control for controlling generation of the pulses at a predetermined RF frequency.

4. The RF source as claimed in claim 1, wherein the controller includes phase lock control for controlling a phase of sequential pulses to a common phase.

5. The RF source as claimed in claim 1, wherein the first RF pulse generator and the second RF pulse generator are arranged to generate pulses at respective different power levels.

6. The RF source as claimed in claim 1, comprising:
a third RF pulse generator.

7. The RF source as claimed in claim 1, further comprising:
an interleaver arranged to receive the RF pulses from the first RF pulse generator and the second RF pulse generator as input pulses and interleave them in order to produce an interleaved signal.

8. A method of operating an RF source for a radiotherapy device comprising a first RF pulse generator and a second RF pulse generator arranged to deliver RF pulses to a particle accelerator, the method comprising:
controlling the first RF pulse generator and the second RF pulse generator to generate pulses sequentially;
controlling the first RF pulse generator to generate pulses under one or more fixed operating conditions; and
altering a pulse-repetition frequency of the second RF pulse generator.

9. The method as claimed in claim 8, comprising:
detecting failure of one of the first RF pulse generator or the second RF pulse generator; and
controlling operation of a non-failed RF pulse generator differentially accordingly.

10. The method as claimed in claim 9, wherein the non-failed RF pulse generator is controlled to operate at least one of a different power level, a different pulse repetition rate, and a different pulse repetition pattern.

11. The method as claimed in claim 8, in which the first RF pulse generator and the second RF pulse generator are controlled to generate pulses at different pulse powers.

12. The method as claimed in claim 8, the method further comprising:
interleaving the RF pulses from the first RF pulse generator and the second RF pulse generator in order to produce an interleaved signal.

13. A radio therapy device comprising an RF source, the RF source comprising:
a first RF pulse generator;
a second RF pulse generator, wherein the first RF pulse generator and the second RF pulse generator are configured to deliver RF pulses to a particle accelerator; and
a controller to:
control the first RF pulse generator and the second RF pulse generator to generate pulses sequentially;
control the first RF pulse generator to generate pulses under one or more fixed operating conditions; and
alter a pulse-repetition frequency of the second RF pulse generator.

14. The radio therapy device of claim 13, wherein the controller includes automatic frequency control for controlling generation of the pulses at a predetermined RF frequency.

15. The radio therapy device of claim 13, wherein the controller includes phase lock control for controlling a phase of sequential pulses to a common phase.

16. The radio therapy device of claim 13, wherein the first RF pulse generator is configured to generate a pulse at a first power level and the second RF pulse generator is configured to generate a pulse at a second power level different than the first power level.

17. A method of operating an RF source for a radiotherapy device comprising a first RF pulse generator and a second RF pulse generator arranged to deliver RF pulses to a particle accelerator, the method comprising:
controlling the first RF pulse generator and the second RF pulse generator to generate a series of interleaved pulses;
controlling the first RF pulse generator to generate pulses under one or more fixed operating conditions;
altering a pulse-repetition frequency of the second RF pulse generator; and
delivering the series of interleaved pulses to the particle accelerator, wherein the first RF pulse generator generates pulses at a first power and the second RF pulse generator generates pulses at a second power.

18. The method of claim 17, wherein the first RF pulse generator and the second RF pulse generator are phase-locked.

19. The method of claim 17, wherein an electron input of the particle accelerator is varied during a radiotherapy treatment fraction session.

20. The method of claim 17, the method further comprising:
using the RF source to generate a radiotherapy treatment beam; and
rotating the radiotherapy treatment beam about a patient.

* * * * *